(12) United States Patent
Bonyak et al.

(10) Patent No.: US 10,182,857 B2
(45) Date of Patent: Jan. 22, 2019

(54) FORCE FEEDBACK DEVICE AND METHOD FOR CATHETERS

(71) Applicant: BIOSENSE WEBSTER (ISRAEL) LTD., Yokneam (IL)

(72) Inventors: Yevgeny Bonyak, Haifa (IL); Dror Shlomo Levy, Irvine, CA (US); Meir Bar-Tal, Haifa (IL); Ronen Krupnik, Karmiel (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/341,432

(22) Filed: Nov. 2, 2016

(65) Prior Publication Data

US 2017/0071663 A1 Mar. 16, 2017

Related U.S. Application Data

(62) Division of application No. 13/795,047, filed on Mar. 12, 2013, now Pat. No. 9,486,272.

(51) Int. Cl.
*A61B 18/14* (2006.01)
*A61B 18/00* (2006.01)
(Continued)

(52) U.S. Cl.
CPC .......... *A61B 18/00* (2013.01); *A61B 18/1233* (2013.01); *A61B 18/1492* (2013.01);
(Continued)

(58) Field of Classification Search
CPC ............ A61B 18/1492; A61B 18/1233; A61B 2018/00577; A61B 2018/00898;
(Continued)

(56) References Cited

U.S. PATENT DOCUMENTS 6,226,542 B1  5/2001  Reisfeld
6,241,724 B1  6/2001  Fleischman
(Continued)

FOREIGN PATENT DOCUMENTS

EP   1 524 586 A1   4/2005
EP   2 574 278 A2   4/2013
(Continued)

OTHER PUBLICATIONS

European Search Report dated Jun. 6, 2014 from corresponding European Patent Application No. 14158738.6.
(Continued)

*Primary Examiner* — William J Levicky

(57) ABSTRACT

The present invention is directed to a method of ablation. The method includes the steps of inserting a probe having an ablation electrode into a body of a living subject and urging the ablation electrode into a contacting relationship with a target tissue. A measurement of a contact force is made between the ablation electrode and the target tissue, and the measurement is haptically communicated to an operator. The probe is adjusted responsively to the communicated measurement, to achieve a desired value of the contact force while ablating the target tissue using the ablation electrode.

7 Claims, 5 Drawing Sheets

(51) Int. Cl.

| | | |
|---|---|---|
| *A61B 5/00* | (2006.01) | |
| *A61B 18/12* | (2006.01) | |
| *A61B 34/00* | (2016.01) | |
| A61B 5/01 | (2006.01) | |
| A61B 5/053 | (2006.01) | |
| A61B 17/32 | (2006.01) | |
| A61B 90/00 | (2016.01) | |
| A61B 34/20 | (2016.01) | |

(52) U.S. Cl.
CPC ............... *A61B 34/76* (2016.02); *A61B 5/01* (2013.01); *A61B 5/053* (2013.01); *A61B 5/0531* (2013.01); *A61B 5/0538* (2013.01); *A61B 5/6852* (2013.01); *A61B 5/6885* (2013.01); *A61B 5/7455* (2013.01); *A61B 17/320068* (2013.01); *A61B 34/20* (2016.02); *A61B 2018/00297* (2013.01); *A61B 2018/00303* (2013.01); *A61B 2018/00357* (2013.01); *A61B 2018/00577* (2013.01); *A61B 2018/00642* (2013.01); *A61B 2018/00821* (2013.01); *A61B 2018/00839* (2013.01); *A61B 2018/00898* (2013.01); *A61B 2034/2051* (2016.02); *A61B 2090/065* (2016.02); *A61B 2218/002* (2013.01); *A61B 2505/05* (2013.01)

(58) Field of Classification Search
CPC ........... A61B 2018/00297; A61B 2018/00636; A61B 5/6885; A61B 5/7455
See application file for complete search history.

(56) References Cited

U.S. PATENT DOCUMENTS

| | | |
|---|---|---|
| 6,301,496 B1 | 10/2001 | Reisfeld |
| 6,695,808 B2 | 2/2004 | Tom |
| 6,814,733 B2 | 11/2004 | Schwartz et al. |
| 6,892,091 B1 | 5/2005 | Ben-Haim |
| 6,915,149 B2 | 7/2005 | Ben-Haim |
| 6,997,924 B2 | 2/2006 | Schwartz et al. |
| 7,156,816 B2 | 1/2007 | Schwartz et al. |
| 7,306,593 B2 | 12/2007 | Keldar et al. |
| 7,536,218 B2 | 5/2009 | Govari et al. |
| 7,756,576 B2 | 7/2010 | Levin |
| 9,289,258 B2 | 3/2016 | Cohen |
| 2004/0006337 A1 | 1/2004 | Nasab et al. |
| 2005/0113167 A1* | 5/2005 | Buchner ................. A63F 13/02 463/30 |
| 2005/0132290 A1 | 6/2005 | Buchner et al. |
| 2006/0235316 A1* | 10/2006 | Ungless ............... A61B 5/0006 600/509 |
| 2007/0100332 A1 | 5/2007 | Paul et al. |
| 2008/0275465 A1 | 11/2008 | Paul et al. |
| 2008/0288038 A1 | 11/2008 | Paul et al. |
| 2009/0024062 A1* | 1/2009 | Einarsson ............. A61B 5/486 600/595 |
| 2009/0090763 A1 | 4/2009 | Zemiok et al. |
| 2010/0073150 A1* | 3/2010 | Olson .................... A61B 34/30 340/407.1 |
| 2010/0168620 A1* | 7/2010 | Klimovitch ............ A61B 5/042 600/587 |
| 2010/0298826 A1 | 11/2010 | Leo et al. |
| 2011/0132378 A1 | 6/2011 | Levendowski et al. |
| 2013/0172784 A1* | 7/2013 | Kirschenman ....... A61B 5/6843 600/587 |
| 2013/0274712 A1 | 10/2013 | Schecter |
| 2013/0321262 A1* | 12/2013 | Schecter .............. A61B 5/7455 345/156 |
| 2014/0100563 A1 | 4/2014 | Govari et al. |
| 2014/0221768 A1* | 8/2014 | Krupnik ............... A61B 5/7455 600/301 |

FOREIGN PATENT DOCUMENTS

| | | |
|---|---|---|
| JP | 06-206191 A | 7/1994 |
| JP | 07-266263 A | 10/1995 |
| JP | 2009-113184 A | 5/2009 |
| JP | 2014-514025 A | 6/2014 |
| KR | 2008 0050705 A | 6/2008 |

OTHER PUBLICATIONS

Haines, David E., M.D., "Determinants of Lesion Size During Radiofrequency Catheter Ablation: The Role of Electrode-Tissue Contact Pressure and Duration of Energy Delivery", Journal of Cardiovascular Electrophysiology, Dec. 1991, pp. 509-515, vol. 2, No. 6.

Japanese Notification of Reasons for Refusal dated Oct. 31, 2017 in corresponding Japanese Application No. 2014-047337.

Russian Search Report dated Feb. 5, 2018 from corresponding Russian Application No. 2014109347.

* cited by examiner

FORCE FEEDBACK DEVICE AND METHOD FOR CATHETERS

CROSS-REFERENCE TO RELATED APPLICATION

This application is a divisional of U.S. patent application Ser. No. 13/795,047, filed Mar. 12, 2013.

BACKGROUND OF THE INVENTION

Field of the Invention

This invention relates to tissue ablation systems. More particularly, this invention relates to monitoring of contact between an invasive probe and tissue within the body.

Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

U.S. Pat. No. 7,306,593, issued to Keidar et al., describes a method for ablating tissue in an organ by contacting a probe inside the body with the tissue to be ablated, and measuring one or more local parameters at the position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

U.S. Patent Application Publication Nos. 2008/0288038 and 2008/0275465, both by Sauarav et al., which are herein incorporated by reference, describe an electrode catheter system, which may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

The document *Determinants of Lesion Size During Radiofrequency Catheter Ablation: The Role of Electrode-Tissue Contact Pressure and Duration of Energy Delivery*, David E. Haines, J. Cardiovasc Electrophysiol, Vol. 2, pp. 509-515, December 1991 described the effects of varying electrode tissue contact pressure and duration of RF energy delivery on the size of the resultant lesion in an in vitro model of canine myocardium. A greater contact force significantly decreased the power required to maintain a constant electrode-tissue interface temperature, and the lesion size grew monoexponentially with time.

U.S. Patent Application Publication No. 2010/0298826 describes a force-time integral for real time estimation of lesion size in catheter-based ablation systems. The apparatus measures the force exerted by a contact ablation probe on a target tissue and integrates the force over an energization time of the ablation probe. The force-time integral can be calculated and utilized to provide an estimated lesion size (depth, volume and/or area) in real time. The force-time integral is said to possibly account for variations in the power delivered to the target tissue in real time to provide an improved estimation of the lesion size.

SUMMARY OF THE INVENTION

Embodiments of the present invention provide a haptic device that is worn on the body of an operator of an ablation system. The device applies direct force to the body using one or more actuators that reflect the contact force between an ablation catheter and target tissue such as the endocardial surface of the heart. The device may be embodied as a wrist bracelet, and can be dimensioned to the order of a standard wrist watch for the comfort and convenience of the operator. Contact data haptically provided to the operator by the device minimizes a need to consult a visual display and avoids distraction caused by an audio alert that might provide the contact information. The sensations produced by the haptic device are perceived by the operator as though a virtual assistant were holding his hand while he performs a medical procedure.

There is provided according to embodiments of the invention an ablation apparatus, including a flexible probe adapted for insertion into a heart of a living subject. The probe has a distally disposed ablation electrode to be brought into contact with a target tissue in the heart, wherein the probe is operative for making a measurement of a contact force between the probe and the target tissue. The apparatus includes a power source, controlled by an operator, which is operative to apply a dosage of energy via the ablation electrode to the target tissue to ablate the target tissue, a transmitter, operative to transmit an indication of the measurement of the contact force, a wearable device having a receiver for receiving signals from the transmitter and an actuator operative to haptically stimulate the operator responsively to the signals.

According to an aspect of the ablation apparatus, the wearable device is a bracelet that includes a processor, and an electromechanical actuator linked to the processor, which is operative for vibrating the bracelet when the contact force reaches a predetermined value.

According to another aspect of the ablation apparatus, vibrating is independently performed on subdivisions of the bracelet, wherein the subdivisions are adapted for approximation to respective locations on a body part of the operator, and wherein the subdivisions comprise inflatable cells, and vibrating is performed by inflating and deflating the cells independently, either pneumatically or hydraulically.

According to a further aspect of the ablation apparatus, vibrating is independently performed on subdivisions of the bracelet, wherein the subdivisions are adapted for approximation to respective locations on a body part of the operator, and wherein the subdivisions comprise inflatable cells containing an electroactive polymer, and are deformed by electrically stimulating the polymer to inflate and deflate selected ones of the cells.

According to an additional aspect of the ablation apparatus, the wearable device is a bracelet, which includes a processor, wherein the actuator deforms the bracelet when the contact force reaches a predetermined value under control of the processor.

According to a further aspect of the ablation apparatus, the bracelet includes a strap adapted to be worn about a wrist of the operator, and the actuator is operative to deform the bracelet by electromechanically varying a tension of the strap.

According to yet another aspect of the ablation apparatus, the bracelet includes an electroactive polymer, and the actuator is operative to deform the bracelet by electrically stimulating the polymer.

According to still another aspect of the ablation apparatus, the bracelet includes an inflatable cell, and the actuator is operative to deform the bracelet by pneumatically or hydraulically inflating and deflating the cell.

According to a further aspect of the ablation apparatus, the bracelet also includes a sensor operative to detect physiological events of the operator and a transmitting module for communicating indications of the events.

There is provided according to embodiments of the invention a method of ablation, which is carried out by inserting a probe having an ablation electrode into a body of a living subject, urging the ablation electrode into a contacting relationship with a target tissue, making a measurement of a contact force between the ablation electrode and the target tissue, haptically communicating the measurement to an operator, and responsively to the communicated measurement, adjusting the probe to achieve a desired value of the contact force while ablating the target tissue using the ablation electrode.

According to one aspect of the method, haptically communicating is performed by providing a cuff, and vibrating the cuff when the contact force reaches a predetermined value.

According to an additional aspect of the method, vibrating includes varying a tension of a strap disposed about a body part of the operator.

According to still another aspect of the method, vibrating is independently performed on subdivisions of the cuff, wherein the subdivisions are approximated to respective locations on a body part of the operator.

According to yet another aspect of the method, the subdivisions of the cuff comprise inflatable cells, and vibrating includes independently inflating and deflating the cells pneumatically or hydraulically.

A further aspect of the method the subdivisions of the cuff comprise inflatable cells containing an electroactive polymer includes inflating and deflating the cells by electrically stimulating the polymer.

An aspect of the method is performed while ablating the target tissue by sensing physiological events of the operator and transmitting indications of the events to a receiver.

There is provided according to embodiments of the invention a method of ablation, which is carried out by inserting a probe having an ablation electrode and a sensing electrode into a body of a living subject, urging the ablation electrode into a contacting relationship with a target tissue, thereafter making a measurement of at least one electroanatomic parameter at the target tissue with the sensing electrode, haptically communicating the measurement to an operator, and responsively to the communicated measurement ablating the target tissue using the ablation electrode.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

The term "couple" or "coupled" is intended to mean either an indirect or direct connection. Thus, if a first device is coupled to a second device, that connection may be through a direct connection, or through an indirect connection via other devices and connections, or via inductive or capacitive coupling.

The term "actuator" as used herein includes but is not limited to an electromechanical actuator. Rather, it includes the effectuating element of the several embodiments disclosed below that haptically stimulate an operator by deforming a cuff and bracelet.

Figure 1:
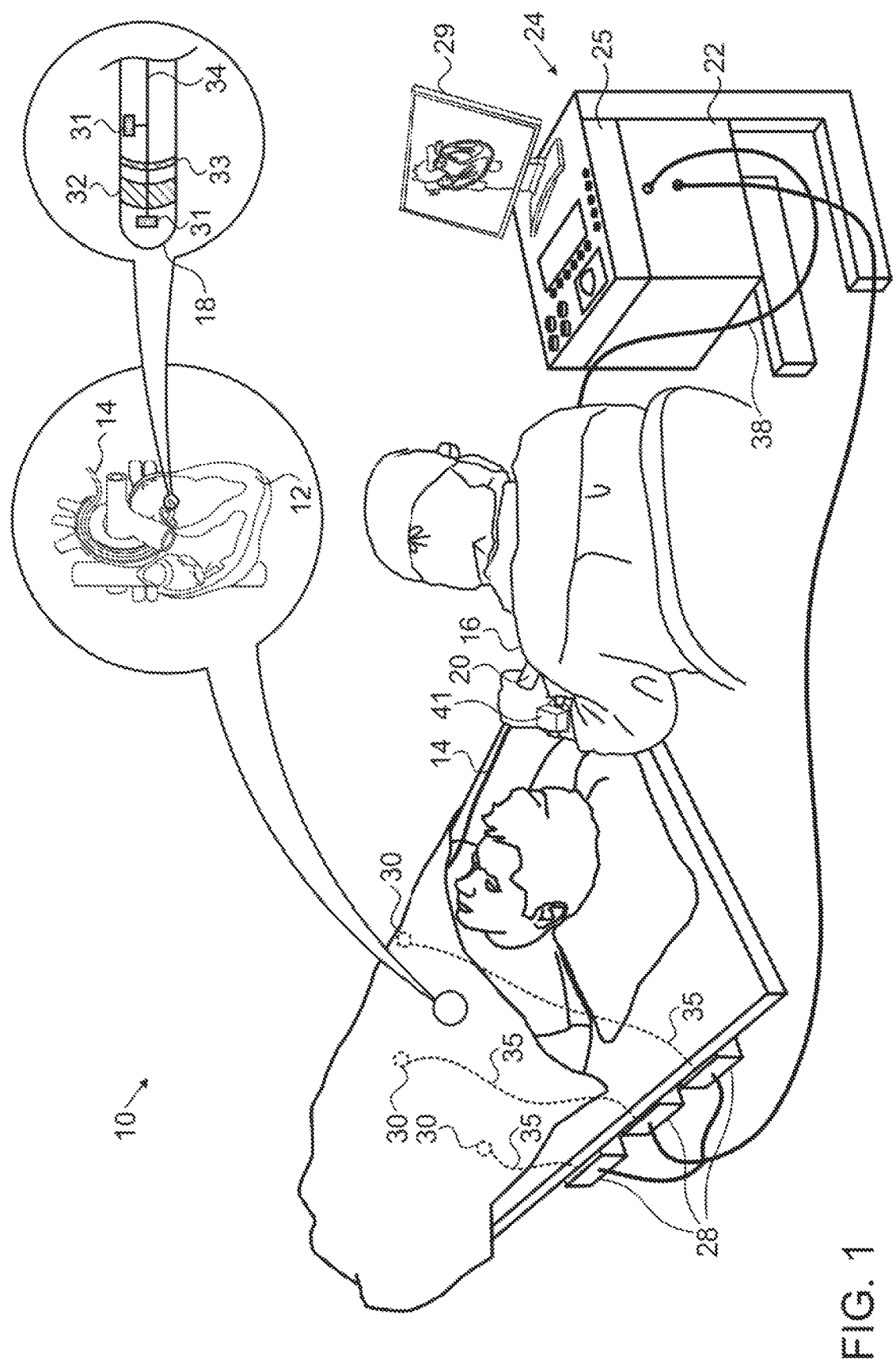
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24, are disposed between the ablation electrodes 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference. A temperature sensor such as thermocouples 31, may be mounted on or near the ablation electrode 32 and optionally or near the sensing electrode 33. The thermocouples 31 are connected to the electrode circuit as described in further detail below.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14, such as contact force. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally placed catheter, which is inserted into the heart 12 and maintained in a fixed position relative to the heart 12. Conventional pumps and lines for circulating liquids through the catheter 14 for cooling the ablation site are provided.

Moreover, the catheter 14, cooperatively with the console 24, provides contact force information to the operator 16, which may be acquired by measuring the phase angle of the impedance as taught in commonly assigned U.S. application Ser. No. 13/648,449 to Govari, which is herein incorporated by reference. Alternatively, contact force data may be obtained by any of the above-mentioned techniques for contact force measurement. In this regard, the THERMO-COOL® SMARTTouch™ Contact Force Catheter, available from Biosense Webster, is suitable for the catheter 14.

The operator 16 is provided with a vibratory haptic device, shown in the example of FIG. 1 as a wrist bracelet 41, which receives communications from a transmitter in the console 24, for example by a wireless communication link. Alternatively, the communications link may be a wired link. Responsively to a message from the console 24, the wrist bracelet 41 generates a haptic notification to the operator 16 of the contact force between the catheter 14 and target tissue, such as an ablation site on the endocardial surface of the heart 12. The wrist bracelet 41 is not limiting. For example a haptic device could be realized in other forms, such as a pad applied to other parts of the body, ankle bracelet, shoe, ring, or collar.

Haptic Device

Figure 2:
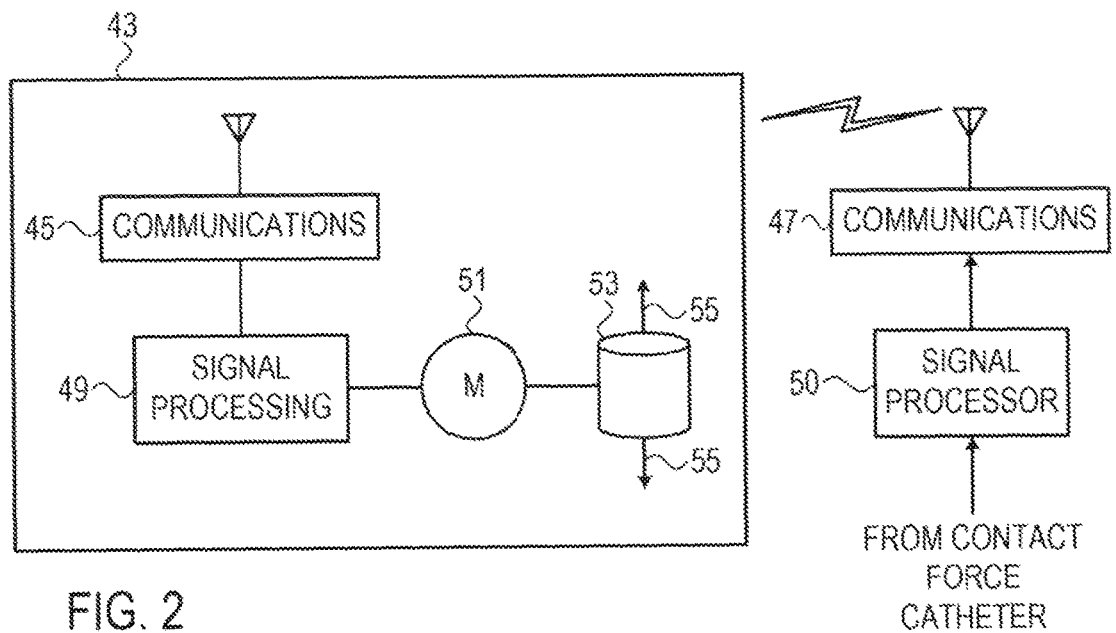
FIG. 2 is a block diagram of a haptic device in accordance with an embodiment of the invention.

Reference is now made to FIG. 2, which is a block diagram of a haptic device 43, which can be realized as the wrist bracelet 41 (FIG. 1), and which is constructed and operative in accordance with an embodiment of the invention.

The haptic device 43 has a wireless communications module 45, which receives signals from another communications module 47. The communications module 47 is linked to the catheter 14 (FIG. 1), generally via a signal processor 50. Telemetry signals produced by the signal processor 50 are reflective of the contact force between the catheter 14 and the target tissue. They are transmitted by the communications module 47 to the communications module 45 using any suitable communications protocol.

The signal processor 49 has control circuitry linked to an electric motor 51, which drives an actuator 53. The actuator 53 has an oscillatory, vibratory or reciprocating motion, indicated by arrows 55. The tactile sensation experienced by the operator and produced by the actuator 53 is representative of the contact force of the catheter as communicated via the communications module 45. In operation, the actuator 53 creates a tactile sensation, which the operator can interpret as a measure of the contact force currently being applied by the catheter 14 against the target tissue. Additionally or alternatively, the signal processor 49 may be configured to control the motor 51 so as to cause the actuator 53 to vibrate, the vibrations being felt with a periodicity by the operator whose strength or period correlates with the contact force. Further alternatively, combinations of the intensity, periodicity and intervals of the vibration may communicate the contact force of the catheter 14 to the operator 16. Vibratory frequencies varying from about 40 Hz to 250 Hz are suitable to communicate different levels of contact force.

For example, the actuator 53 may vibrate rapidly or slowly according to contact force levels, or may alternate between vibrating and not vibrating to produce tactile silence for perceptibly longer periods, the pattern encoding levels of contact force. In a further example, the actuator 53 may operate for a relatively long and perceptible interval, e.g., 0.25-2 sec, and then cease to operate for a similar interval. Alternatively, specific ranges may produce different sensations, for example as a "step function" of the contact force. Encoding of activity patterns of the actuator 53 in various other ways will occur to those skilled in the art. In any case, such patterns, when haptically perceived by the operator, indicate the magnitude of the catheter's contact force (or other parameter). Additionally or alternatively, the patterns might constitute, for example, a binary signal, indicating whether or not the catheter is in a stable location. The signals may be configurable by the operator, who may choose the kind of feedback he prefers to tactilely receive.

Figure 3:
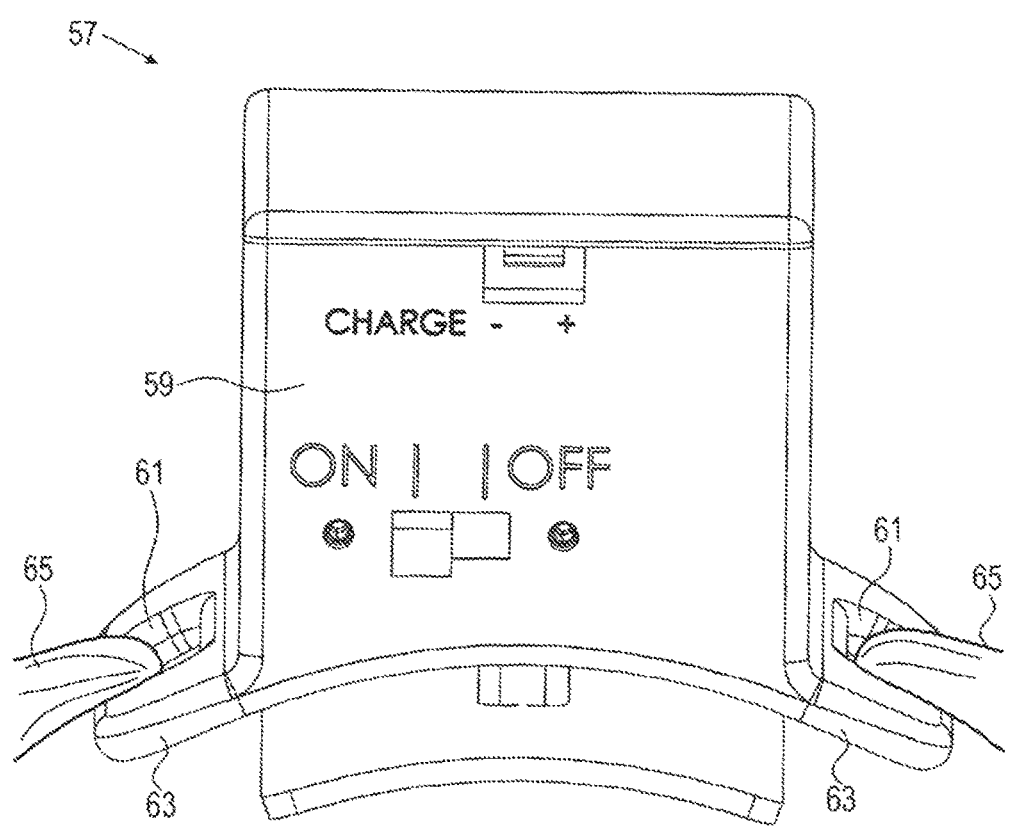
FIG. 3 is a frontal elevation of a haptic device shown in slight perspective, in accordance with an embodiment of the invention.

Reference is now made to FIG. 3, which is a frontal elevation of a haptic device 57 in slight perspective, in accordance with an embodiment of the invention. The haptic device 57 has a housing 59 that encloses components to be described below. Slots 61 formed through side projections 63 accommodate straps 65 for securing the haptic device 57 around a part of the body of the operator, such as the wrist.

Figure 4:
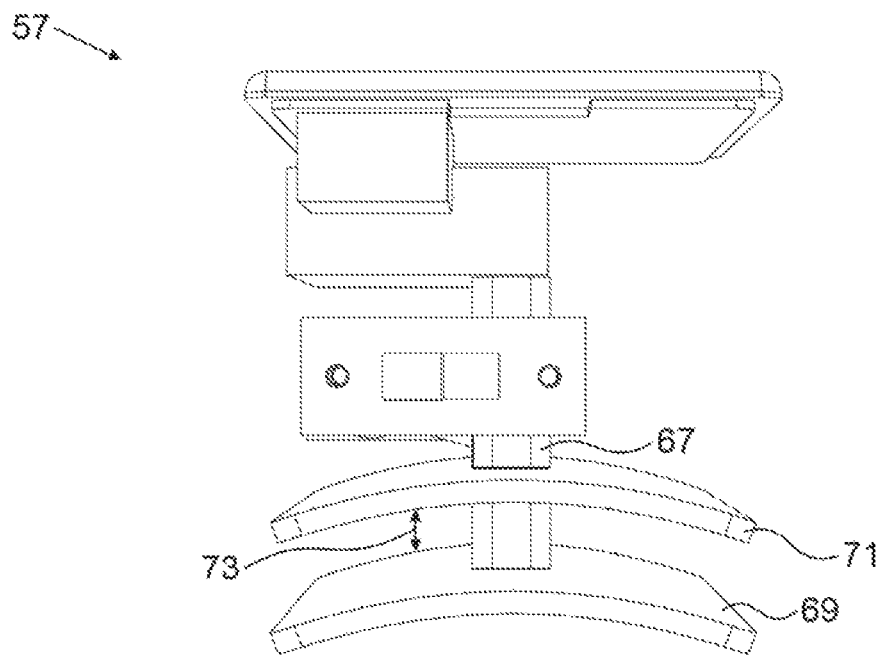
FIG. 4 is a frontal elevation of the haptic device shown in FIG. 3, with the housing removed and shown in slight perspective, in accordance with an embodiment of the invention.

Reference is now made to FIG. 4, which is a frontal elevation of the haptic device 57 with the housing removed and shown in slight perspective, in accordance with an embodiment of the invention. A linear actuator 67 moves pad 69 away from a pad 71, and reciprocates it toward the pad 71 as indicated by arrow 73. The motion imparted by the actuator 67 manipulates the strap 65, and shortens or lengthens the effective length of the strap 65 (FIG. 3) according to whether the pad 69 moves away from or toward the pad 71. The tension or change in the effective length of the strap 65 is in proportion to the force applied to the wrist or other body part.

Suitable linear actuators are available, from Pololu Corporation, 920 Pilot Rd., Las Vegas, Nev. 89119. Actuators of this type may include limit switches (not shown). They may also include a feedback potentiometer to enable closed-loop position control.

Figure 5:
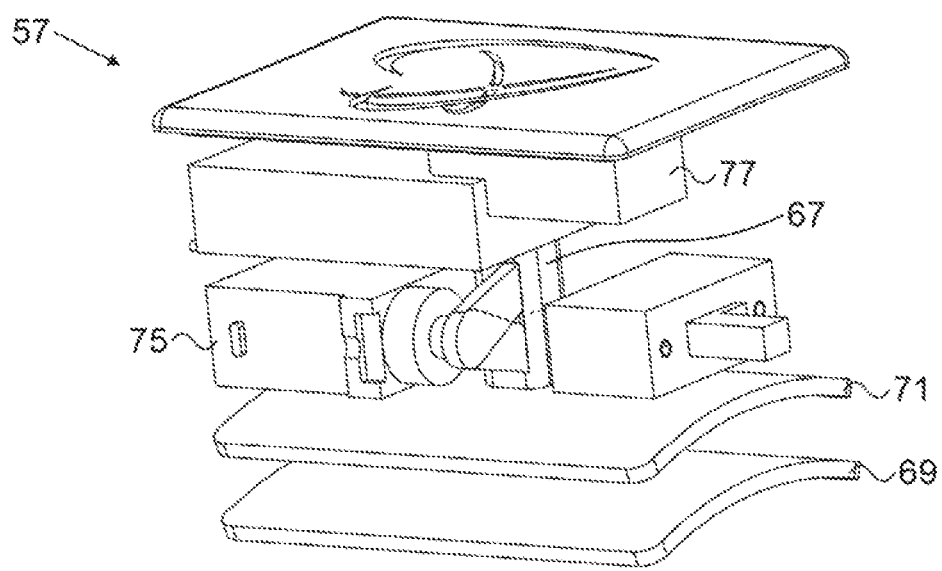
FIG. 5 is a side elevation of the haptic device shown in FIG. 3 with the housing removed and shown in slight perspective, in accordance with an embodiment of the invention.

Reference is now made to FIG. 5, which is another elevation of the haptic device 57 with the housing removed, shown in slight perspective, in accordance with an embodiment of the invention. This view shows a motor 75 that drives the actuator 67. The communications and signal processing modules described with reference to FIG. 2 are housed in an enclosure 77.

This embodiment provides a single tactile channel for communicating a parameter of interest, e.g., contact force, to the operator 16 (FIG. 1). By time multiplexing the channel, other parameters of interest may also be communicated. Examples of such other parameters are given below in the discussion of the First Alternate Embodiment.

First Alternate Embodiment

Figure 6:
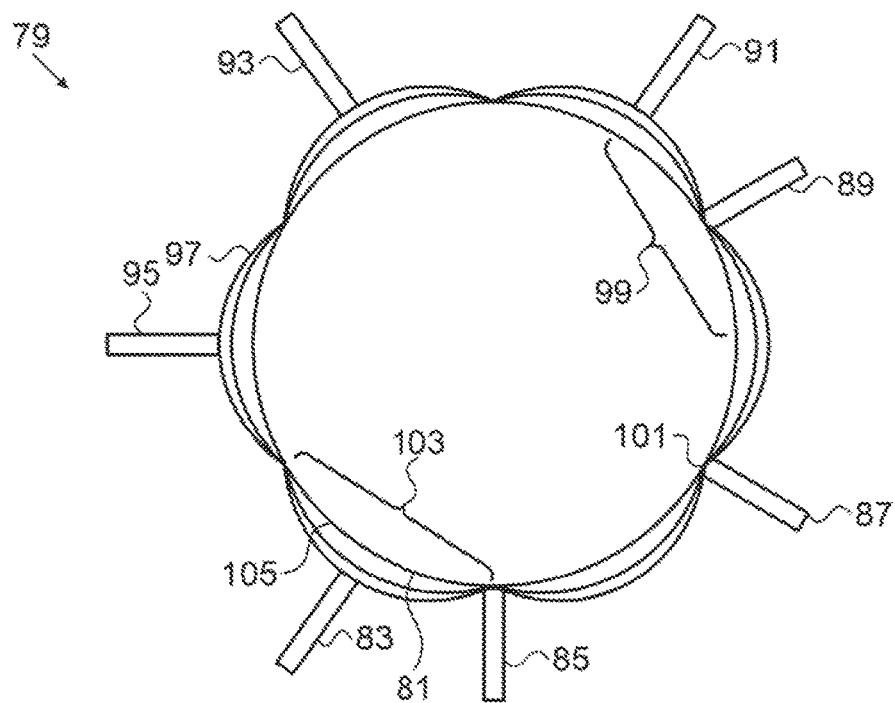
FIG. 6 is a schematic view of portions of a haptic device being worn about a wrist of an operator, in accordance with an alternate embodiment of the invention.

Reference is now made to FIG. 6, which is a schematic view of portions of a haptic device 79 being worn about a wrist 81 of an operator, in accordance with an alternate embodiment of the invention. This embodiment operates in a similar manner to the embodiment described with respect to FIG. 2-FIG. 5. However the single actuator 67 is replaced by an array of actuators 83, 85, 87, 89, 91, 93, 95, which are distributed along the length of a strap 97 that is wrapped about wrist 81. The actuators are independently controlled as described above, e.g., by multiplexing the communication channel between the communications modules 45, 47 (FIG. 2) or by providing a plurality of communication channels. The actuators 83, 85, 87, 89, 91, 93, 95 are thus capable of individually and independently applying pressure at points on the circumference of the wrist 81 or other body part. For example, in FIG. 6 the actuator 89 is active, depressing a segment 99 of the strap 97, and thus producing an enhanced tactile sensation on the wrist generally at a point 101, while the actuator 83 is inactive, and a corresponding segment 103 of the strap 97 is lax and is not strongly perceived by the operator. Hence the operator would not have a meaningful tactile sensation in the neighborhood of a point 105 opposite the actuator 83.

An advantage of this embodiment is an ability to communicate a plurality of electroanatomic parameters of interest to the operator, either sequentially or concurrently. The actuators 83, 85, 87, 89, 91, 93, 95 may be respectively assigned to different parameters. For example, one of the actuators could alert the operator to a myocardial activation time of interest at a point of contact between the catheter 14 and the endocardium of the heart 12. Another actuator might signal the presence at the point of contact of a micro-reentry pattern of myocardial electrical propagation. In other non-limiting examples, a tactile indication of ablation site temperature might cause the operator to vary the flow of irrigation fluid through the catheter 14. A tactile alarm indicating imminent or actual expiration of a time interval of interest, e.g., an interval during which an ablator is energized.

Second Alternate Embodiment

Figure 7:
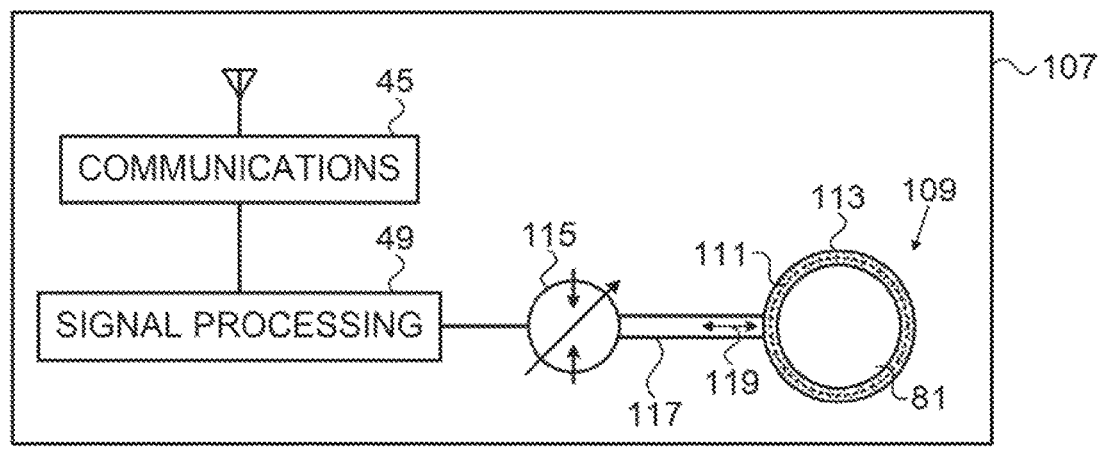
FIG. 7 is a schematic view of portions of a haptic device being worn about a wrist of an operator, in accordance with an alternate embodiment of the invention.

Reference is now made to FIG. 7, which is a schematic view of portions of a haptic device 107 being worn about the wrist 81, in accordance with an alternate embodiment of the invention. This embodiment has components in common with the haptic device 43 (FIG. 2), but operates using hydraulic or pneumatic methods to produce a tactile effect on the wrist 81. An inflatable cuff 109 (indicated by hatching in FIG. 7) is adapted to fit about the wrist 81 (or other body part), and is expandable from a deflated configuration indicated by broken line 111 to an inflated configuration indicated by solid line 113.

Inflation and deflation are produced by the action of a displacement hydraulic motor 115, which can be bidirectional, as shown in FIG. 7, or unidirectional. The motor operates under control of the signal processor 49, as described above with respect to FIG. 2.

When the hydraulic motor 115 inflates the cuff 109 through a hydraulic line 117, the operator perceives a pressure sensation beneath the cuff, which disappears when the cuff 109 deflates, either actively when the hydraulic motor 115 is bidirectional, or passively when the hydraulic motor 115 is unidirectional. Fluid flow into and out of the cuff 109 is indicated by arrow 119.

In this embodiment the cuff 109 may be constructed of hollow rubber or plastic. A module that includes the communications module 45, signal processor 49 and hydraulic motor 115 may be worn on a belt about the operator's waist, and the hydraulic line 117 may be small-diameter flexible tubing. The cuff 109 may be disposable.

Third Alternate Embodiment

Figure 8:
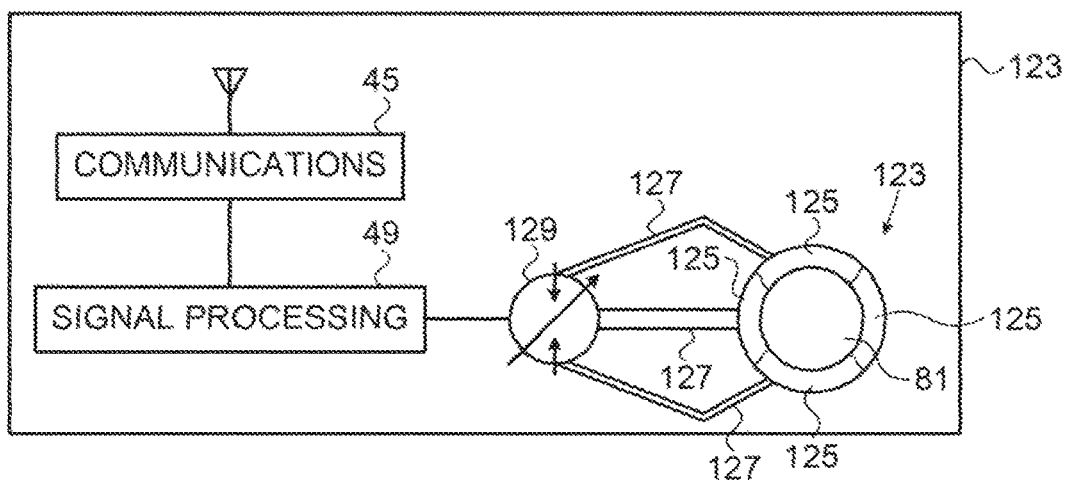
FIG. 8 is a schematic view of portions of a haptic device being worn about a wrist of an operator, in accordance with an alternate embodiment of the invention.

Reference is now made to FIG. 8, which is a schematic view of portions of a haptic device 121 being worn about the wrist 81, in accordance with an alternate embodiment of the invention. This embodiment has components in common with the haptic device 107 (FIG. 7). However a cuff 123 is partitioned into multiple cells 125, each supplied by separate hydraulic lines 127. A hydraulic motor 129 may have individually operated ports or valves as shown in FIG. 8. Alternatively, individual hydraulic motors may supply the cells 125 via respective hydraulic lines 127. In any case, the hydraulic motor 129 or motors are controlled by the signal processor 49.

This embodiment has the same enhanced abilities as the haptic device 79 (FIG. 6), which are not repeated in the interest of brevity.

Fourth Alternate Embodiment

Figure 9:
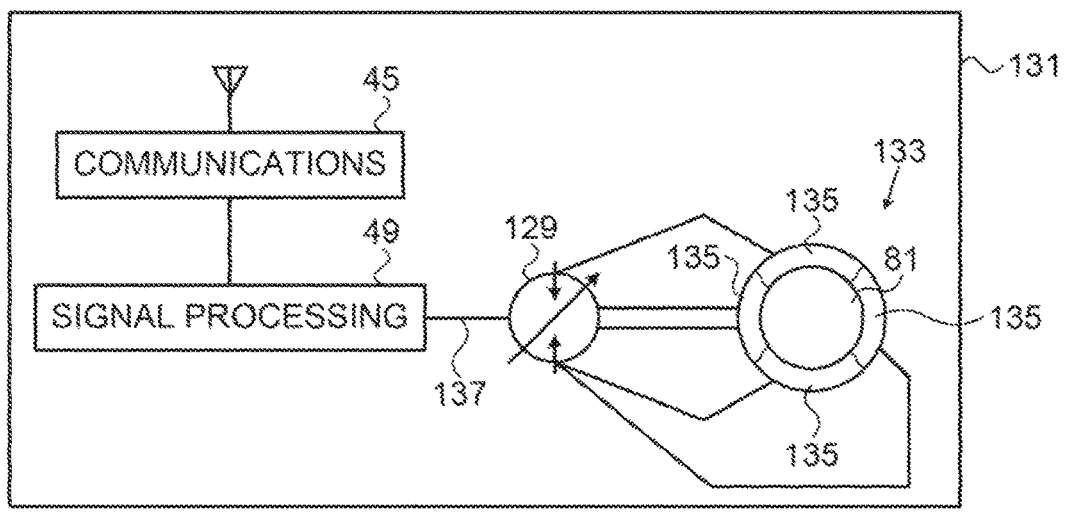
FIG. 9 is a schematic view of portions of a haptic device being worn about a wrist of an operator, in accordance with an alternate embodiment of the invention.

Reference is now made to FIG. 9, which is a schematic view of portions of a haptic device 131 being worn about the wrist 81, in accordance with an alternate embodiment of the invention. In this embodiment, a deformable bracelet or cuff 133 has one or more cells 135 containing a shape-changing electroactive polymer, which when appropriately stimulated by signals from the signal processor 49 via electrical cable 137, cause the cells 135 to individually and independently deform. The timing and pattern of the deformations is sensed by the operator as explained above.

Fifth Alternate Embodiment

Figure 10:
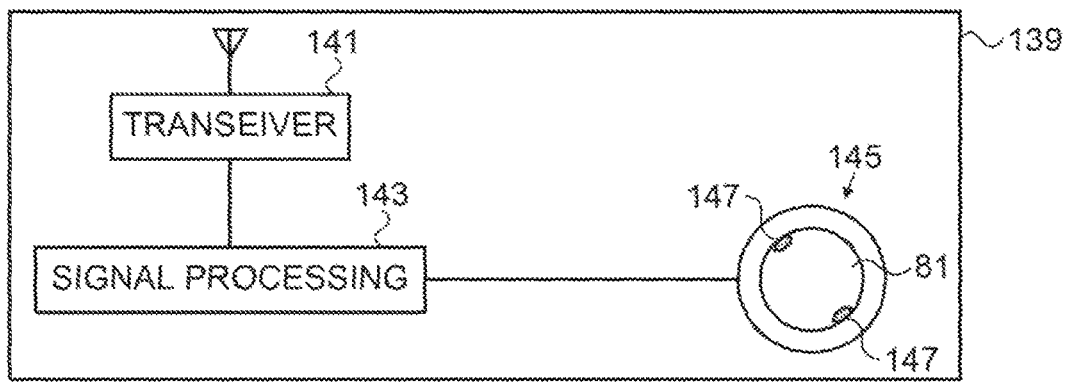
FIG. 10 is a schematic view of portions of an enhanced haptic device being worn about a wrist of an operator, in accordance with an alternate embodiment of the invention.

Reference is now made to FIG. 10, which is a schematic view of portions of an enhanced haptic device 139 being worn about the wrist 81, in accordance with an alternate embodiment of the invention.

In this embodiment the communications module described above is replaced by a transceiver 141, enabling the haptic device 43 to confirm receipt of information transmitted from the communications module 47 (FIG. 2) and to send data and command signals to the communications module 47. The transceiver 141 is linked to a signal processing unit 143.

The haptic device 139 includes a cuff 145 linked to the signal processing unit 143. The cuff 145 may be constructed according to any of the above-described embodiments. The cuff 145 is augmented by one or more sensors 147, which are linked to the signal processing unit 143. The signal processing unit 143 adapted to process signals from the sensors 147 and relay them to the transceiver 141, which then communicates them to the console 24 (FIG. 1).

The sensors 147 may be constructed to detect various physiological and chemical data of the operator, for example sweat, blood chemistry, heart rate and rhythm, or even an electrocardiogram. Additionally or alternatively, some of the sensors 147 may be location sensors, which could detect, for example, the position of the operator's hand during the procedure.

This embodiment facilitates evaluation of the operator's skills and the effectiveness of the procedure by correlation of data obtained from the operator with data obtained from the ablation catheter. Additionally or alternatively, the sensory data may cause the operator to modify or terminate the procedure when predetermined criteria are met.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of ablation, comprising the steps of:
   inserting a probe into a body of a living subject, the probe having an ablation electrode;
   urging the ablation electrode into a contacting relationship with a target tissue;
   making a measurement of a contact force between the ablation electrode and the target tissue;
   haptically communicating the measurement to an operator via a wearable device, the wearable device having a transceiver integrated therein for receiving signals from, and transmitting signals to, a first communications module remote from the wearable device, the wearable device further having and an actuator integrated therein, the actuator operatively connected to the transceiver and operative to haptically stimulate the operator responsively to the signals such that the degree of the haptic stimulation experienced by the operator correlates to the amount of the contact force; and
   responsively to the communicated measurement, adjusting the probe to achieve a desired value of the contact force while ablating the target tissue using the ablation electrode.

2. The method according to claim 1, wherein the wearable device is a cuff.

3. The method according to claim 2, wherein vibrating comprises varying a tension of a strap disposed about a body part of the operator.

4. The method according to claim 2, wherein vibrating is independently performed on subdivisions of the cuff, wherein the subdivisions are approximated to respective locations on a body part of the operator.

5. The method according to claim 4, wherein the subdivisions of the cuff comprise inflatable cells, and vibrating comprises independently inflating and deflating the cells pneumatically or hydraulically.

6. The method according to claim 4, wherein the subdivisions of the cuff comprise inflatable cells containing an electroactive polymer, further comprising inflating and deflating the cells by electrically stimulating the polymer.

7. The method according to claim 1, further comprising the step of: while ablating the target tissue, sensing physiological events of the operator via a sensor in the wearable device and transmitting indications of the events to a receiver.

* * * * *